US00PP10869P

United States Patent [19]

Bull

[11] Patent Number: Plant 10,869

[45] Date of Patent: Apr. 27, 1999

[54] NEW GUINEA IMPATIENS PLANT NAMED 'REBECCA'

[76] Inventor: Norbert Bull, Gaertnersiedlung 2, Goennebek, Germany

[21] Appl. No.: 08/897,985

[22] Filed: Jun. 23, 1997

[30] Foreign Application Priority Data

Nov. 20, 1996 [DE] Germany ..... IM 418

[51] Int. Cl.[6] ..... A01H 5/00

[52] U.S. Cl. ..... Plt./318

[58] Field of Search ..... Plt./87.6, 318

[56] References Cited

U.S. PATENT DOCUMENTS

P.P. 8,360 8/1993 Bull ..... Plt./87.6

P.P. 8,397 9/1993 Kientzler ..... Plt./87.6

P.P. 8,406 10/1993 Trees ..... Plt./87.6

OTHER PUBLICATIONS

GTITM UPOVROM Citation for 'Rebecca' as per AU PBR 94237, Dec. 20, 1994.

*Primary Examiner*—Howard J. Locker
*Assistant Examiner*—Kent L. Bell
*Attorney, Agent, or Firm*—Foley & Lardner

[57] ABSTRACT

A new and distinct cultivar of New Guinea Impatiens plant named 'Rebecca', characterized by its bright red flower color, medium to large, round flowers, medium green foliage with red veins, low plant habit with medium vigor, and early flowering response.

1 Drawing Sheet

The present invention comprises a new and distinct cultivar of New Guinea Impatiens, referred to by the cultivar name 'Rebecca'.

'Rebecca' is a product of a planned breeding program and was originated from a hybridization made by the inventor Norbert Bull in a controlled breeding program in Goennebek, Germany, in 1993. The female parent was a seedling designated No. 16 and the male parent was a seedling designated No. 1. Both parents are proprietary cultivars used in the breeding program.

'Rebecca' was discovered and selected as one flowering plant within the progeny of the stated cross by the inventor in 1994 in a controlled environment in Goennebek, Germany.

The first act of vegetative or asexual reproduction of 'Rebecca' was accomplished when cuttings were taken from the initial selection in Autumn 1994 in a controlled environment in Goennebek by, or under the supervision of, Norbert Bull.

Horticultural examination of plants grown from these cuttings initiated in Spring 1995 in Goennebek, Germany, and continuing thereafter, has demonstrated that the combination of characteristics as herein disclosed for 'Rebecca' are firmly fixed and are retained through successive generatons of asexual reproduction.

'Rebecca' has not been observed under all possible environmental conditions. The phenotype may vary significantly with variations in environment such as temperature, light intensity and day length, without, however, any variation in genotype.

The following observations, measurements, and comparisons describe plants grown in Hillscheid, Federal Republic of Germany under greenhouse conditions which approximate those generally used in commercial practice.

The following traits have been repeatedly observed and are determined to be basic characteristics of 'Rebecca', which in combination distinguish this impatiens as a new and distinct cultivar:

1. Bright red flower color
2. Medium to large, round flowers
3. Medium green foliage with red veining
4. Low plant habit, medium vigor
5. Early flower response
6. Resistant to powdery mildew Of the many commercial cultivars known to the present inventor, the most similar in comparison to 'Rebecca' are the cultivars 'Karina' (unpatented) and 'Lanai'(U.S. Plant Pat. No. 8,397). In comparison to 'Karina', 'Rebecca' has smaller leaves and is generally more resistant under outdoor conditions.

In comparison to 'Lanai', 'Rebecca' has flowers which are similar in color, but the flowers of 'Rebecca' are somewhat larger and almost flat, in contrast to the distinctly cup-shaped flowers of 'Lanai'.

The accompanying colored photographic drawing shows typical flower and foliage characteristics of 'Rebecca', with colors being as true as possible with illustrations of this type. In this regard, the illustration may not depict the color designations and descriptions as they accurately appear in the botanical description.

In the following description color references are made to The Royal Horticultural Society Colour Chart. The color values were determined indoors from flowers taken from plants grown in Hillscheid, Federal Republic of Germany, under greenhouse conditions which approximate those generally used in commercial practice.

The description is based on plants which were planted as rooted cuttings in 10 cm pots in early March and then grown in a greenhouse at 20° C. minimum temperature.

Classification:

*Botanical.*—A hybrid of the genus Impatiens.

*Commercial.*—New Guinea Impatiens cv 'Rebecca'.

Plant

A. General appearance and form:

*Habit.*—Compact, low, medium wide, very well branched, uniformly mounded, and growth is indeterminate, although weak after flowering begins.

*Height.*—10 cm.

*Width.*—28 cm.

*Internode length.*—25–30 cm.

*Stem color.*—Red to brownish red.

*Flowering response.*—6 weeks after planting of rooted cuttings.

*Flowering season.*—Generally indeterminate, mainly from March to October, depending on light intensity.
*Lasting quality of the bloom.*—About four weeks.
*Propagation.*—Usually terminal tips for cuttings.
*Rooting.*—Color is R.H.S. 159 B-C; roots initiate in about 18 days at 22° C., from sticking to transplanting.

B. Foliage:
*Leaf arrangement.*—Primarily in whorls.
*Shape of leaf.*—Narrow, elliptic, with acute base and accuminate tip.
*Margin.*—Slightly serrated, ciliated.
*Leaf, length.*—About 135 mm.
*Leaf, width.*—About 35 mm.
*Main color of upper surface.*—Medium green, approximately R.H.S. 137 B.
*Veins on upper surface, color.*—Light red to dark pink at the base and light green from the base to the tip.
*Variegation on leaf.*—Absent.
*Main color of lower surface.*—Light green, about 138 B R.H.S.
*Veins on lower surface, color.*—Dark red, about R.H.S. 60 A.
*Petiole, color.*—Medium to dark red, about R.H.S. 60 A B.
*Petiole, length.*—About 15 mm.

Inflorescence

A. Flower:
*Flower number per node.*—About 6, in various stages of development, usually one flower per leaf.
*Form of corolla.*—5 petals per flower.
*Shape.*—Mostly flat, horizontal, upper petal is slightly curved in young plants, slightly zygomorph.
*Average length.*—65 mm.
*Average width.*—63 mm.
*Color* (*general tonality from a distance of three meters*).—Scarlet red.
*Petal number.*—Five (5).
*Petal shape.*—Cordate (heart-shaped), moderately lobed.
*Petal size.*—Length is about 30 mm; width is about 36 mm for upper petals, about 20 mm for lower petals, and about 18 mm for side petals.
*Petal texture.*—Smooth, slightly glossy.
*Petal aspect.*—Mostly flat, horizontal.
*Main color of upper surface.*—R.H.S. 42 A.
*Eye zone.*—Very weak, purple, about R.H.S. 66 B.
*Spur, color.*—Dark red, R.H.S. 53 D.
*Spur shape and size.*—Downward curved, about 45 mm in length.
*Pedicel, length.*—About 35–40 mm.
*Pedicel, color.*—Brownish red, lighter than R.H.S. 60 A.

B. Reproductive organs:
*Androecium.*—Stamens: Five (5) in number, fused, upper surface color is mainly R.H.S. 46 B. Anthers: Hooded, color is about R.H.S. 11 D. Pollen: Color is about R.H.S. 4 D.
*Gynoecium.*—Stigma and style: Five (5) in number, very short, color is about R.H.S. 11D. Ovary: Five (5) celled, 3–5 mm in length, surface color is R.H.S. 137 B-C.

I claim:

1. A new distinct cultivar of New Guinea Impatiens plant named 'Rebecca', as illustrated and described.

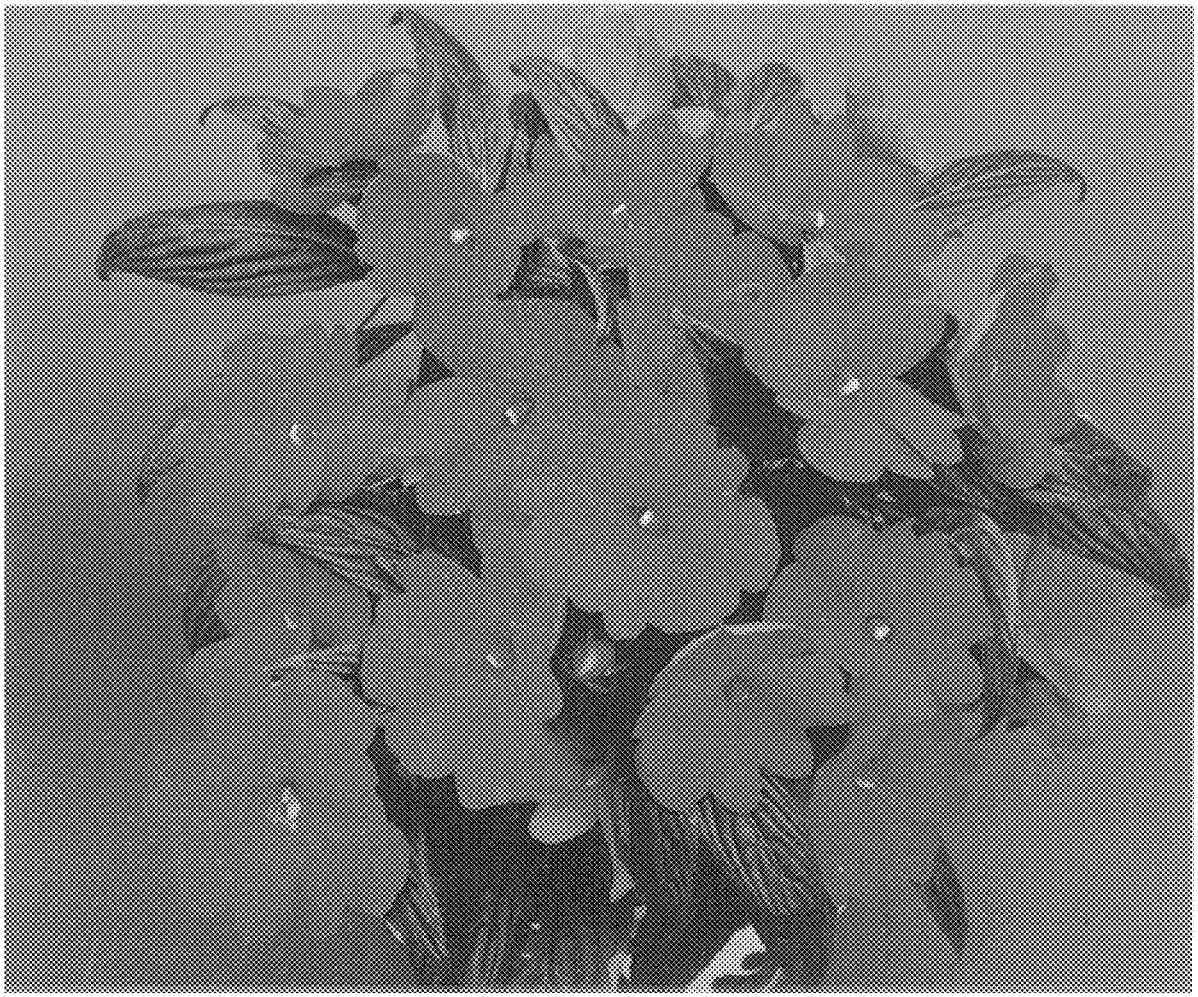

* * * * *